United States Patent
Almishari

(10) Patent No.: US 11,253,542 B2
(45) Date of Patent: Feb. 22, 2022

(54) METHODS OF TREATING VIRAL INFECTIONS

(71) Applicant: Ibrahim Saud Almishari, Durrat Al Bahrain (BH)

(72) Inventor: Ibrahim Saud Almishari, Durrat Al Bahrain (BH)

(*) Notice: Subject to any disclaimer, the term of this patent is extended or adjusted under 35 U.S.C. 154(b) by 1 day.

(21) Appl. No.: 16/848,055

(22) Filed: Apr. 14, 2020

(65) Prior Publication Data

US 2021/0315925 A1    Oct. 14, 2021

(51) Int. Cl.
| | |
|---|---|
| *A61K 33/00* | (2006.01) |
| *A61P 31/12* | (2006.01) |
| *A61B 5/01* | (2006.01) |
| *A61F 7/00* | (2006.01) |
| *A61H 33/02* | (2006.01) |
| *A61K 9/00* | (2006.01) |

(52) U.S. Cl.
CPC ............... *A61K 33/00* (2013.01); *A61B 5/01* (2013.01); *A61F 7/00* (2013.01); *A61H 33/02* (2013.01); *A61K 9/0078* (2013.01); *A61P 31/12* (2018.01); *A61F 2007/0018* (2013.01); *A61F 2007/0029* (2013.01); *A61F 2007/0039* (2013.01); *A61F 2007/0059* (2013.01); *A61F 2007/0063* (2013.01)

(58) Field of Classification Search
None
See application file for complete search history.

(56) References Cited

U.S. PATENT DOCUMENTS

| | | |
|---|---|---|
| 4,942,868 A | 7/1990 | Vago |
| 2008/0173311 A1 | 7/2008 | Miller et al. |
| 2016/0175550 A1 | 6/2016 | Taylor |
| 2017/0296463 A1 | 10/2017 | Minton et al. |

OTHER PUBLICATIONS

World Health Organization ("Clinical management of severe acute respiratory infection when Middle East respiratory syndrome coronavirus (MERS-CoV) infection is suspected", Jan. 2019, WHO/MERS/Clinical/15.1 Revision 1) hereinafter WHO. (Year: 2019).*

Crawford ("Why, When, and How to Bathe a Fever Patient", The American Journal of Nursing, Feb. 1910, vol. 10, No. 5 (Feb. 1910), pp. 314-317). (Year: 1910).*

WHO ("Clinical management of severe acute respiratory infection (SARI) when COVID-19 disease is suspected. Interim guidance V 1.2" (Year: 2020).*

V. Racaniello, Columbia University, "Viral Pathogenesis", <http://www.columbia.edu/itc/hs/medical/pathophys/id/2009/viralpathNotes.pdf>, pulled from web on Apr. 20, 2020; 19 pages.

International Search Report and Written Opinion for International Application No. PCT/IB/21/00239, International Filing Date Apr. 13, 2021, dated Aug. 12, 2021, 10 pages.

Hsiao et al.; "Measurement of body temperature to prevent pandemic COVID-19 in hospitals in Taiwan: repeated measurement Is necessary"; Apr. 9, 2020; [retrieved from the internet on Jul. 20, 2021 (Jul. 20, 2021) at <https://www.journalofhospitalinfection.com/article/S0195-6701 (20)30179-1/fulltext>, 2 pages.

Aw; "The Non-Contact Handheld Cutaneous Infra-red Thermometer for Fever Screening During the COVID-19 global emergency" (Aw) Feb. 21, 2020, [retrieved from the Internet on Jul. 2, 2021 at <htlps://www.journalofhospitalinfeclion.com/article/S0195-6701 (20)30058-XJfulltext>, 1 page.

Lum et al.; "Managing dengue fever in primary care: A practical approach" Aug. 31, 2014, retrieved from the internet an Jul. 20, 2021 at <https://www.ncbi.nlm.nlh.gov/pmc/articles/PMC4399402/>, 9 pages.

Yang et al.; "The preventive strategies of community hospital in the battle of fighting pandemic COVID-19 in Taiwan" Mar. 20, 2020 {retrieved from the internet on Jul. 20, 2021, at <https://www.sciencedirect.com/science/article/pii/S 1684118220300797?vla%3Dihub>, 3 pages.

DOUGHERTY; "How to Take Your Temperature to Check for a Fever -COVID-19, Health Topics"; Hackensack Meridian Health; Mar. 31, 2020, retrieved from the internet on Jul. 20, 2021 at <https://www.hackensackmeridianhealth.org/HealthU/2020/03/31/how-to-take-your-temperature-to-check-for-a-fever/>, 8 pages.

* cited by examiner

*Primary Examiner* — Quanglong N Truong
(74) *Attorney, Agent, or Firm* — Dickinson Wright PLLC; Mark E. Scott

(57) ABSTRACT

Methods of treating viral infections. At least one example embodiment is a method including: measuring a core temperature of a human patient; testing the human for the presence of a virus that causes disease; responsive to the human having both fever and presence of the virus, submerging at least a trunk and legs of the human in water comprising a surfactant, the human at least partially submerged in the water for a treatment period of at least three hours; and controlling a temperature of the water during the treatment period.

17 Claims, No Drawings

METHODS OF TREATING VIRAL INFECTIONS

CROSS-REFERENCE TO RELATED APPLICATIONS

Not Applicable.

BACKGROUND

Viral pathogens may enter the body through a variety of pathways. For example, viral pathogens may enter the body through the respiratory tract. The body attempts to protect against entry through the respiratory tract by way of the mucous membranes and ciliated cells in the nose an upper portions of the respiratory tract. Viral pathogens trapped or captured prior to entry into the lungs are carried into the throat and then into the alimentary tract (e.g., stomach and intestines).

Many viral pathogens cannot survive the relatively harsh environment of the alimentary tract. That is, many viral pathogens captured in the respiratory tract and directed to the alimentary tract, and viral pathogens that enter the alimentary tract directly (e.g., through food) are neutralized in the alimentary tract. However, other viral pathogens can and do survive in the alimentary tract, and thus the alimentary tract represents another pathway through which viral pathogens enter the body. For example, some enteric coronaviruses can withstand the relatively harsh environment of the alimentary tract, and thus enter the body through the stomach and/or intestinal walls.

Generally, the skin is a barrier to most viral pathogens. However, some viral pathogens enter the body is through the skin. For example, dengue virus is known to enter the body directly through the skin. Specifically, the dengue virus infects skin keratinocytes, and also infects and replicates inside the Langerhans cells. Even for viral pathogens for which the skin is a barrier, apertures through the skin (e.g., cuts, sores, abrasions, and bug bites) may allow viral pathogens access to the underlying vascular and lymphatic system.

Regardless of the entry point into the body, viral pathogens may spread within the body through many pathways. For example, some viral pathogens spread throughout the body by way of the blood stream (e.g., hematogenous spread). Other viral pathogens may spread along neural pathways. For example, some coronavirus varieties spread along neural pathways, such as the olfactory pathways.

SUMMARY

At least one example embodiment is directed to a method of treating disease in a human, the method comprising: measuring a core temperature of the human; testing the human for the presence of a virus that causes disease; responsive to the human having both fever and presence of the virus, submerging at least a trunk and legs of the human in water comprising a surfactant, the human at least partially submerged in the water for a treatment period of at least three hours; and controlling a temperature of the water during the treatment period.

The example method may further comprise releasing from the water an airborne substance for inhalation into the lungs. The releasing may comprise releasing at least one selected from a group comprising: nitric oxide; a surfactant suitable for cause a virucidal effect within the lung.

In the example method testing the human may further comprise testing for the presence of severe acute respiratory syndrome 2 (SARS-CoV-2).

In the example method testing the human may further comprise testing for Dengue virus.

In the example method controlling the temperature may further comprise maintaining the temperature above 90 degrees Fahrenheit and below 99 degrees Fahrenheit as long as the core temperature of the human indicates a fever below a predetermined threshold. The predetermined threshold may be 104 degrees Fahrenheit when the human is below an age of 10 years. The predetermined threshold may be 101 degrees Fahrenheit when the human is above an age of 10 years. Further in the example method, controlling the temperature may further comprise chilling the water if the core temperature of the human meets or exceeds the predetermined temperature.

In the example method, submerging the human may further comprise submerging the arms, legs, and trunk of the human. Submerging the human may further comprise partially submerging the head of the human.

In the example method, the surfactant may be at least one selected from a group comprising: soap; and detergent.

In the example method, the surfactant may comprise a virucide. The surfactant may be present in a virucidaly effective amount.

The example may further comprise periodically wetting portions of the human above a water line of the water. Periodically wetting may further comprise covering portions of the human above the water line with a cloth wetted with the water and surfactant.

Other example embodiments are methods comprising treating coronavirus disease in a human. The treating may include: receiving a core temperature measurement of the human; receiving a test result regarding the presence of a Severe Acute Respiratory Syndrome 2 (SARS-CoV-2) virus; responsive to the human having both fever and presence of the SARS-CoV-2 virus, directing that at least a trunk and legs of the human be submerged in water comprising a surfactant, the surfactant having a concentration sufficient to be therapeutically effectively as a virucide, and the human at least partially submerged in the water for a treatment period of at least three hours; and controlling a temperature of the water during the treatment period.

DEFINITIONS

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ."

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various example embodiments are directed to a holistic approach to reducing or eliminating viral infections. More particularly, an example embodiment is directed to treating disease caused by coronavirus. More particularly still, an example embodiment is directed to treating Covid-19, the disease caused infection with severe acute respiratory syndrome 2 (SARS-CoV-2). Example embodiments include assisting the body's immune response by reducing or eliminating viral pathogens on and within the body at locations where the immune system has reduced or no effect, such as on the skin. More particularly still, in patients with active viral infections and active and ongoing immune response (e.g., fever, dry cough), example embodiments are directed to reducing or eliminating viral pathogen reentry by at least partially submerging the body of the patient in water comprising a virucidal component, the submergence for an extended treatment period. The specification first turns to a discussion of viral pathogens, including entry points into to the body and dissemination within the body, to orient the reader.

As discussed briefly in the Background section above, viral pathogens may enter the body through a variety of pathways. The pathways through which viral pathogens enter may include the respiratory tract, the alimentary tract, the urogenital tract, the eyes, and the skin. With respect to entry through the respiratory tract, the body attempts to reduce such entry by trapping or capturing the viral pathogens by way of the mucous membranes and ciliated cells. Viral pathogens captured are carried to the throat and swallowed. Those viral pathogens that make it past the mucous membranes and ciliated cells may thus infect the soft tissue of the lungs. The viral pathogens that are captured and swallowed enter the stomach and intestines (i.e., the alimentary tract).

Many viral pathogens cannot survive the relatively harsh environment of the alimentary tract. For example, the stomach is acidic and contains bile detergents to assist with digestion. The acidity and bile detergents break down many viral pathogens, leaving them as harmless proteins. However, other viral pathogens can and do survive in the alimentary tract, and thus the alimentary tract represents another pathway through which viral pathogens enter the body. In fact, some coronaviruses can withstand the relatively harsh environment of the alimentary tract, and thus enter the body through the stomach and/or intestinal walls.

Another pathway through which viral pathogens enter the body is the skin. Some viral pathogens, such as dengue virus associated with Dengue fever, enter through the skin directly. Even if the skin acts as a barrier to a viral pathogen generally, apertures through the skin (e.g., cuts, sores, abrasions, punctures, and bug bites) may allow viral pathogens access to the underlying tissue and thus serve as a pathway into the body.

Regardless of the entry point, viral pathogens may spread within the body through many pathways. Some viral pathogens spread along neural pathways within the body. For example, some coronavirus varieties spread along neural pathways, such as the olfactory pathways. Viral pathogens may also spread by way of the lymphatic system, and from within the lymphatic system may have access to the bloodstream. It follows that viral pathogens may also spread within the body by way of the blood stream (e.g., hematogenous spread or viremia).

Viremia is considered to have two categories—primary viremia and secondary viremia. Primary viremia refers to replication of the viral pathogen close to or at the primary entry point into the body. The replicated viral pathogens then spreads throughout the body through the blood stream. Secondary viremia refers to replication and release of the viral pathogens from locations within the body accessed by viral pathogens from the primary viremia. Thus, once a body is infected with a viral pathogen, that viral pathogen may have physical access to the entire body through the various routes of dissemination.

Viral pathogens have varying ability to infect host cells. Some viral pathogens have the ability only to infect (i.e., invade and replicate within) cells within the intestinal tract. Other viral pathogens have the ability to infect only the soft tissue of lungs. Further still, some viral pathogens have the ability to infect only cells of the nervous system. However, yet still other viral pathogens may infect many different types of cells, and are referred to as pantropic. For example, some coronavirus varieties are known to be pantropic. It follows that for pantropic viruses, regardless of entry point into the body, once within the body and disseminated, replication of the viral pathogens may be found almost anywhere within the body. It further follows that an infected person can pass along the viral pathogen to others in many forms. For example, the viral pathogens may be transmitted within spittle during conversations, coughing, or even just exhalation. Viral pathogens that find their way to skin (e.g., through sweat glands, open sores, cuts, or abrasions) can be transferred by direct touching, or through intermediate surfaces such as door handles.

Example embodiments disclosed herein include assisting the body's immune response by reducing or eliminating viral pathogens. More particularly, in patients with active viral infections and active and ongoing immune response (e.g., fever, dry cough), example embodiments are directed to reducing or eliminating viral pathogen reentry into the body. The specification first turns to a description of the example method, and then provides a non-limiting theoretical explanation of the effect.

In particular, example embodiments are directed to treating a human patient that has an active viral pathogen infection. In one example, the patient has an active viral pathogen infection as well an active immune response, such as running a fever. Example embodiments may measure a core temperature of the patient, the measurement in any suitable form. Moreover, the patient is tested for presence of the virus that causes the disease (e.g., tested for the SARS CoV-2 virus that causes the disease Covid-19, or tested for the dengue virus that causes Dengue fever). Responsive to the patient having both a fever and the viral pathogen, the patient is at least partially submerged in water comprising a virucidal and/or surfactant. The patient remains fully or partially submerged for an extended treatment period. In some cases, the treatment period may be between and including one hour and six hours, and in some cases between and including two hours and four hours.

The submerging may take many forms. In some cases, at least the trunk and legs of the patient are submerged. In other cases, the arms, legs, and trunk of the patient are submerged. With proper respiration mechanisms, the patient may be fully submerged. In example embodiments, the portions of the patient's body (e.g., the face and head) above the water line are periodically wetted. For example, the portions of the patient's body above the water line may be covered with a cloth wetted with water, the virucide, and/or the surfactant. In some cases the wetting of the cloth is by way of the water within which the patient is partially submerged, but such is not required. The wetting may take place at any suitable frequency to ensure the exposed portions are frequently wetted (e.g., every three to five minutes).

During the extended treatment period, the temperature of the water may be controlled or maintained for the comfort of the patient. In some cases, the temperature of the water is controlled so as not to induce hyperthermia. Likewise, so as not to suppress the patient's immune response, in some cases the temperature of the water is controlled so as not to unduly reduce the fever of the patient. In some cases, controlling the temperature may comprise maintaining the temperature above 90 degrees Fahrenheit and below 99 degrees Fahrenheit as long as the core temperature of the patient indicates a fever below a predetermined threshold. The predetermined threshold may be different for different patients. For example, if the patient is below the age of 10 years, the predetermined threshold may be a suitable temperature for children, such as 104 degrees Fahrenheit. On the other hand, adults may not tolerate well, and may have unwanted secondary effects, from high fever and thus in some cases if the patient above the age of 10 years, and more particularly above the age of 15 years, the predetermined threshold may 101 degrees Fahrenheit.

The controlling of the water temperature of the previous paragraph assumes that the patient's body can adequately maintain the fever as part of the immune response. However, in some patients the fever as part of the immune response may rise above a safe temperature, and thus in yet still further embodiments controlling the temperature of the water may further involve chilling the water if the core temperature of the patient meets or exceeds the predetermined threshold. For example, for children below the age of 10 years, the water may be chilled if the core temperature of the patient exceeds 104 degrees Fahrenheit. Similarly, for adults, the water may be chilled if the core temperature of the patient exceeds 101 degrees Fahrenheit.

As discussed above, the water may comprise a virucide and/or surfactant. Any suitable virucide and/or surfactant may be used, and in fact many surfactants in a therapeutically sufficient amount have virucidal properties. For example, when a surfactant is used, the surfactant may be soap alone, detergent alone, or a combination of soap and detergent. The virucide likewise may take any suitable form. In the context of submerging the patient in water with a virucide, the water may thus include a therapeutically sufficient amount of iodine, isopropyl alcohol, or ethanol, singly or in combination. In some cases, the water comprises both a virucide and a surfactant that alone or combination are present in a therapeutically sufficient amount. For those portions of the body above the water line, the wetting may including periodically wetting with a virucide that may differ from the virucide of the water.

The specification now provides an explanation for the effect. What is provided below is a theoretical explanation for the reduction or elimination of viral pathogens within the body caused by use of the example methods. While much is known in the field of virology regarding viral pathogen invasion of the body, cell infection and replication, and dissemination within the body (e.g., primary and secondary viremia), there are still many unknowns. The explanation provided is thus one possible explanation for the effects, but should not be read as a limitation as to the underlying mechanism of operation.

Based on the current body of knowledge regarding the SARS-CoV-2 virus and the related Covid-19 disease, as well as based on the current body of knowledge regarding coronavirus in non-human mammals, one possible explanation for the spread of the virus is that during an active viral pathogen infection the patient is subjected to significant "reinfection." Reinfection in this context does not mean a separate and distinct viral infection at a later date; rather, reinfection in this context refers to the viral pathogens re-entering the body during an active infection, which thus increases the overall viral load with which the patient's immune system must be responsive. In particular, the skin may represent a major reinfection factor during an active viral pathogen infection (e.g., SARS-CoV-2, and the dengue virus). The reinfection factor associated with the skin may take many forms, such as the skin as point of reentry, and/or the skin as starting point for reentry through other pathways.

Consider, as an example, that a pantropic virus may be replicating in many different types of cells throughout the patient's body, and that at least some of the virus finds its way to the skin. For example, during cold sweats associated with fever the virus may be secreted from sweat glands. As another example, the exocrine glands within the skin may secrete oily or waxy matter, sometimes referred to as sebum, that may also contain the virus. In addition to, or in place of, such viral pathogens emerging from the skin, viral pathogens may be deposited on the skin, such as by sneezing, coughing, talking, or poor hygiene associated with urination and bowl movements. Thus, the skin may host a significant number of viral pathogens. The skin-based viral pathogens may thus be transferred to clothes and bedsheets.

In some cases, the skin may be a reentry point (e.g., for dengue virus, or through cuts, sores, abrasions, punctures, and bug bites for other viral pathogens). In other cases, the reinfection factor may be the viral pathogens on the skin re-entering through other pathways, such as the through the lungs and/or through the alimentary tract. For example, a patient with viral pathogens on the skin may inadvertently touch the face, nose, or mouth, causing reentry and thus increased viral load. The viral pathogens deposited onto sheets and bedclothes may become airborne, as sheets are adjusted or inspiratory airflow moves through contaminated fabric. Moreover, the possible reentry points are not mutually exclusive—the viral pathogen may be reentering through some or all the reentry points, not only directly increasing the viral load, but also increasing the secondary viral load based on later replication of the reentered viral pathogens. Such reentry directly increases in viral load, and also indirectly increases viral load in the form of a second wave of viral pathogen infection, in some cases three to four hours after the primary infection is addressed by the immune system. Unchecked, the cycle may continue repeatedly. Similar to viremia, in many cases the secondary infection may have a larger or greater viral load than the primary infection. In many cases, the immune response of the patient may be overwhelmed by the viral load when replication and dissemination associated with the secondary infection occurs.

Thus, the example methods may reduce or eliminate reinfection associated with the skin, whether that reinfection mechanism is direct (e.g., direct reentry through the skin), indirect (e.g., the skin as the source of the viral pathogen reentry through other entry pathways), or both. In particular, by fully or partially submerging the patient in water with a virucide and/or surfactant, any viral pathogens that find their way to the skin (through any mechanism) are effectively eliminated before having the opportunity to reenter the patient. The viral load on the patient is thus reduced, and in fact the second peak of the viral load (e.g., secondary viremia) may be reduced or eliminated. With a lower viral load to address, the patient's immune system may thus be able to keep pace, having sufficient antibodies to tag the viral pathogens within the body and enabling the white blood cells to destroy such tagged viral pathogens.

In many cases a single treatment session may be sufficient to enable the patient's body to address the viral pathogen infection. However, in some cases, perhaps depending on how early the treatment was performed in relation to the infection and the onset of patient's immune response, a second or third treatment may be used. During treatment, the patient's clothing, handled with personal protective equipment, should be washed thoroughly with soap and dried prior to being used again to avoid the clothing being a reinfection modality.

The water in which the patient is submerged, in addition to suppressing reinfection caused by skin factors, may also contain or produce an inhalable substance (e.g., released by effervescence) to treat the lungs in some form. For example, the substance that creates effervescence may release nitric oxide and/or other surfactants that work within the lungs to break down viral pathogens found on the air-side of the areola.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method of treating disease in a human, the method comprising:
    measuring a core temperature of the human, the core temperature indicating fever;
    testing the human for the presence of a virus that causes disease, the testing indicating presence of the virus;
    submerging at least the trunk and legs of the human in water comprising a surfactant, the human at least partially submerged in the water for a treatment period of at least three hours; and
    controlling the temperature of the water during the treatment period.

2. The method of claim 1 further comprising releasing from the water an airborne substance for inhalation into the lungs.

3. The method of claim 2 wherein releasing further comprises releasing at least one selected from a group comprising: nitric oxide; a surfactant suitable for cause a virucidal effect within the lung.

4. The method of claim 1 wherein testing the human further comprises testing for the presence of severe acute respiratory syndrome 2 (SARS-CoV-2).

5. The method of claim 1 wherein testing the human further comprises testing for Dengue virus.

6. The method of claim 1 wherein controlling the temperature further comprises maintaining the temperature above 90 degrees Fahrenheit and below 99 degrees Fahrenheit as long as the core temperature of the human indicates a fever below a predetermined threshold.

7. The method of claim 6 wherein the predetermined threshold is 104 degrees Fahrenheit when the human is below an age of 10 years.

8. The method of claim 6 wherein the predetermined threshold is 101 degrees Fahrenheit when the human is above an age of 10 years.

9. The method of claim 6 wherein controlling the temperature further comprises chilling the water if the core temperature of the human meets or exceeds the predetermined temperature.

10. The method of claim 1 wherein submerging the human further comprises submerging the arms, legs, and trunk of the human.

11. The method of claim 10 wherein submerging the human further comprises partially submerging the head of the human.

12. The method of claim 1 wherein the surfactant is at least one selected from a group comprising: soap; and detergent.

13. The method of claim 1 wherein the surfactant comprises a virucide.

14. The method of claim 13 wherein the surfactant is present at a virucidally effective amount.

15. The method of claim 1 further comprising periodically wetting portions of the human above a water line of the water.

16. The method of claim 15 wherein periodically wetting further comprises covering portions of the human above the water line with a cloth wetted with the water and surfactant.

17. A method comprising:
    treating coronavirus disease in a human by
        receiving a core temperature measurement of the human, the core temperature indicates the presence of fever;
        receiving a test result regarding the presence of a Severe Acute Respiratory Syndrome 2 (SARS-CoV-2) virus, the test result indicating presence of SARS-CoV-2 in the human;
        directing that at least a trunk and legs of the human be submerged in water comprising a surfactant, the surfactant having a concentration sufficient to be therapeutically effectively as a virucide, and the human at least partially submerged in the water for a treatment period of at least three hours; and
        controlling the temperature of the water during the treatment period.

* * * * *